(12) United States Patent
Silverman et al.

(10) Patent No.: US 9,416,106 B2
(45) Date of Patent: Aug. 16, 2016

(54) 2-AMINOPYRIDINE-BASED SELECTIVE NEURONAL NITRIC OXIDE SYNTHASE INHIBITORS

(71) Applicant: Northwestern University, Evanston, IL (US)

(72) Inventors: Richard B. Silverman, Winnetka, IL (US); Qing Jing, Morton Grove, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/840,801

(22) Filed: Aug. 31, 2015

(65) Prior Publication Data

US 2015/0368201 A1    Dec. 24, 2015

Related U.S. Application Data (62) Division of application No. 14/199,599, filed on Mar. 6, 2014, now Pat. No. 9,120,750.

(60) Provisional application No. 61/774,147, filed on Mar. 7, 2013.

(51) Int. Cl.
*C07D 401/00* (2006.01)
*C07D 213/73* (2006.01)
*C07D 401/12* (2006.01)
*C07D 401/14* (2006.01)

(52) U.S. Cl.
CPC ............ *C07D 213/73* (2013.01); *C07D 401/12* (2013.01); *C07D 401/14* (2013.01)

(58) Field of Classification Search
CPC .......................... C07D 401/12; C07D 401/14
USPC ....................................................... 546/278.4
See application file for complete search history.

(56) References Cited

U.S. PATENT DOCUMENTS

| | | | |
|---|---|---|---|
| 7,470,790 B2 | 12/2008 | Silverman et al. | |
| 2002/0045656 A1 | 4/2002 | Chenard et al. | |
| 2002/0151572 A1 | 10/2002 | Lowe, et al. | |
| 2013/0040359 A1 | 2/2013 | Silverman et al. | |

FOREIGN PATENT DOCUMENTS

| | | |
|---|---|---|
| WO | 9910339 A1 | 3/1999 |
| WO | 0050400 A1 | 8/2000 |

OTHER PUBLICATIONS

Jing et al. Bioorganic & Medicinal Chemistry Letters (2013), 23(20), 5674-5679.*
Holden et al., "Structural and biological studies on bacterial nitric oxide synthase inhibitors", Proceedings of the National Academy of Sciences of the United States of America, 2013, 110(45), 18127-18131.
Wegener et al., "Nitric Oxide Synthase Inhibitors as Antidepressants", Pharmaceuticals, 2010, 3, 273-299.
International Search Report and Written Opinion from PCT/US2014/021366, mailed Jul. 24, 2014, 9 pages.

* cited by examiner

*Primary Examiner* — Nizal Chandrakumar
(74) *Attorney, Agent, or Firm* — Reinhart Boerner Van Deuren s.c.

(57) ABSTRACT

Aminopyridine compounds, as can be used in conjunction with methods for modulation of nitric oxide synthase activity.

6 Claims, 2 Drawing Sheets

2-AMINOPYRIDINE-BASED SELECTIVE NEURONAL NITRIC OXIDE SYNTHASE INHIBITORS

This application is a divisional of and claims priority to and the benefit of application Ser. No. 14/199,599 filed Mar. 6, 2014 and issued as U.S. Pat. No. 9,120,750 on Sep. 1, 2015, which claimed priority to and the benefit of prior provisional application Ser. No. 61/774,147 filed Mar. 7, 2013—each of which is incorporated herein by reference in its entirety.

This invention was made with government support under GM049725 awarded by the National Institutes of Health. The government has certain rights in the invention.

BACKGROUND OF THE INVENTION

Neuronal nitric oxide synthase (nNOS) catalyzes the oxidation of L-arginine to L-citrulline in the central nervous system, generating nitric oxide (NO), a critical neurotransmitter. Significant research has implicated the overexpression of nNOS—and overproduction of NO—in various neurological diseases, including Parkinson's, Alzheimer's, and Huntington's diseases, as well as neuronal damage due to stroke, cerebral palsy and migraine headaches. Inhibiting endothelial nitric oxide synthase (eNOS) and inducible nitric oxide synthase (iNOS) is, however, undesirable, because these isozymes are responsible for maintaining crucial body function. Thus, selective inhibition of nNOS over its closely related isoforms, eNOS and iNOS, can provide a promising strategy in developing therapeutics for the treatment of neurodegenerative diseases.

Many organic scaffolds have been investigated over the past decade. Some compounds exhibit good potency and high selectivity, but suffer from poor bioavailability, thereby hampering their therapeutic potential. Yet other compounds, while promising, are limited by synthetic challenge and/or low yield. As a result, there remains an on-going concern in the art to provide an efficient approach toward a facile synthesis of a wide range of such compounds, with structures optimized for enhanced pharmacological effect.

SUMMARY OF THE INVENTION

In light of the foregoing, it is an object of the present invention to provide compounds, compositions and related methods of use for the selective inhibition of neuronal nitric oxide synthase, thereby overcoming various deficiencies and shortcomings of the prior art including those outlined above. It would be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide one or more small molecule and/or non-peptide compounds exhibiting selective nNOS inhibition over other enzyme isoforms and providing improved membrane permeability and bioavailability.

It can be another object of the present invention to provide one or more such compounds incorporating moieties found in natural amino acids and other natural products, to optimize pharmacological profile.

It can be another object of the present invention, alone or in conjunction with one or more of the preceding objectives, to provide a versatile synthetic route for incorporation of such naturally-derived moieties into compounds comprising one or more aminopyridine moieties shown effective in promoting selective nNOS inhibition.

It can be another object of the present invention to provide one or more such compounds for in vitro use and study under conditions promoting nitric oxide production, indicative of one or more mammalian disease states.

Alternatively, it can also be an object of the present invention to provide one or more such compounds enabling in vivo treatment of such disease states.

Other objects, features, benefits and advantages of the present invention will be apparent from this summary and the following descriptions of certain embodiments of such compounds, compositions and/or methods and will be readily apparent to those skilled in the art having knowledge of the synthetic techniques described herein. Such objectives, features, benefits and advantages will be apparent from the above as taken into conjunction with the accompanying examples, data, figures and references incorporated herein, together with all reasonable inferences to be drawn therefrom.

In part, the present invention can be directed to compounds of a formula wherein $R^1$ can be selected from 6-amino-4-methylpyridin-2-yl and 6-aminopyridin-2-yl moieties; X can be selected from $CH_2O$ and $CH_2CH_2$ moieties; Y can be selected from O and $CH_2$ moieties; and n can be selected from 1 and 2, and salts, hydrates and solvates thereof.

In part, the present invention can also be directed to compounds of a formula wherein X can be selected from N and CH; L can be selected from $O(CH_2)_n$ and $CH_2NH(CH_2)_n$ moieties, and where n can be selected from 1-3; and $R^1$ can be selected from amino, pyridinyl, piperidinyl, phenyl, fluorophenyl and chlorophenyl moieties, and salts, hydrates and solvates thereof.

In part, the present invention can also be directed to compounds of a formula wherein $R^1$ can be selected from 6-aminopyridin-2-yl, 6-amino-4-methylpyridin-2-yl, phenyl, fluorophenyl and chlorophenyl moieties; $R^2$ can be selected from H, methyl and ethyl moieties; and L can be selected from $CH_2O$, $CH_2CH_2$, $CH_2N$, $CH_2O(CH_2)_2O$, $(CH_2)_5$ and $CH_2N(CH_2)_2N$ moieties, and salts, hydrates and solvates thereof.

In part, the present invention can also be directed to compounds of a formula together with salts, hydrates and solvates thereof.

Regardless, the compounds of this invention are without stereochemical limitation. As illustrated and discussed below, such compounds and/or their intermediates are available as racemic mixtures from which isomers can be resolved, or are diastereomers from which the corresponding enantiomers can be separated. Accordingly, any stereocenter can be (S) or (R) with respect to any other stereocenter(s). As a separate consideration, various compounds can be present as an acid salt, either partially or fully protonated. In certain such embodiments, the counterion(s) can be a conjugate base of a protic acid. Further, it will be understood by those skilled in the art that any one or more the compounds of this invention can be provided as part of a pharmaceutical composition comprising a pharmaceutically-acceptable carrier component for use in conjunction with a treatment method or medicament.

In part, the present invention can also be directed to a method inhibiting, modulating or otherwise affecting a nitric oxide synthase. Such a method can comprise providing a compound of this invention, whether or not part of a pharmaceutical composition, and administering an effective amount of such a compound for contact with a nitric oxide synthase, such compounds including but not limited to those illustrated by the following examples, referenced figures and/or accompanying synthetic schemes. In certain such embodiments, such a compound and/or combination thereof can be present in an amount at least partially sufficient to selectively inhibit neuronal nitric oxide synthase over inducible and endothelial isoforms.

BRIEF DESCRIPTION OF THE DRAWINGS

FIG. 1. Chemical structures of representative, non-limiting inhibitor compounds, in accordance with certain embodiments of this invention.

FIG. 2. Schematic chemical structures of representative, non-limiting selective nNOS inhibitors—also in accordance with this invention.

DETAILED DESCRIPTION OF CERTAIN EMBODIMENTS

Figure 1:
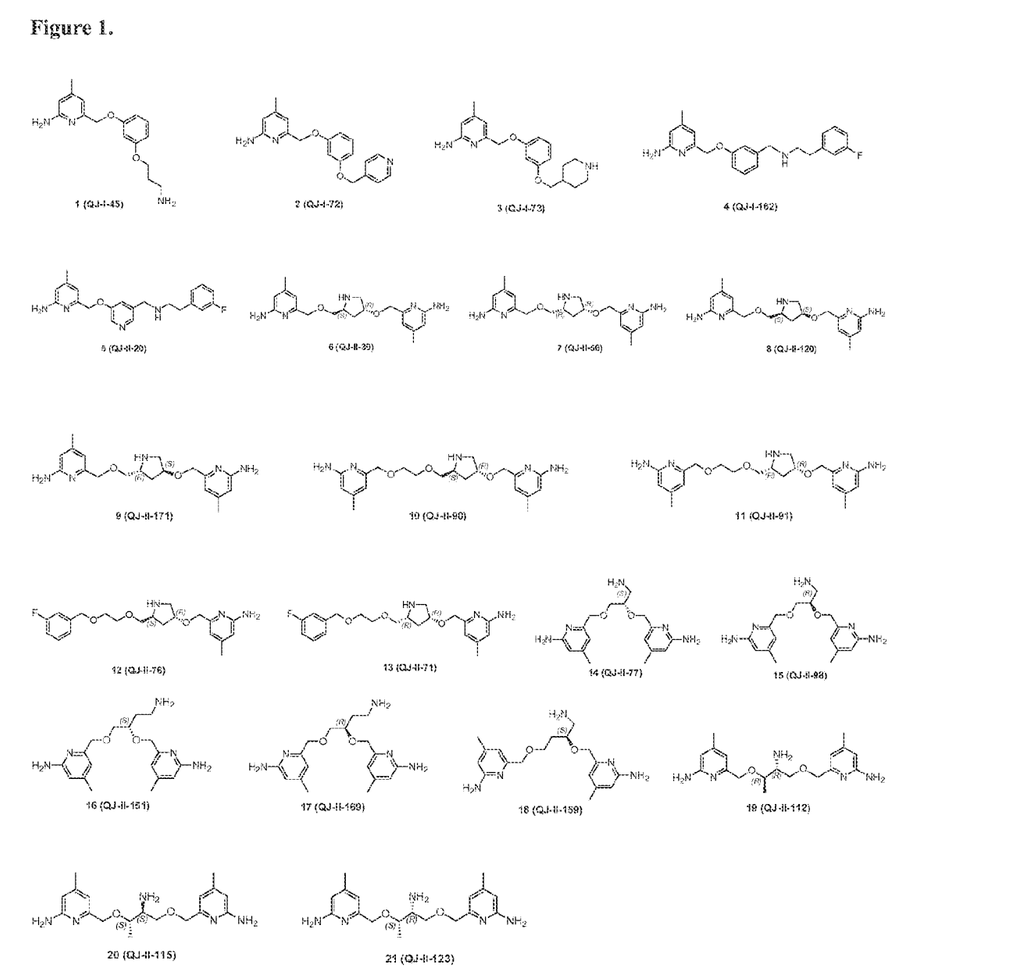
Figure 2:
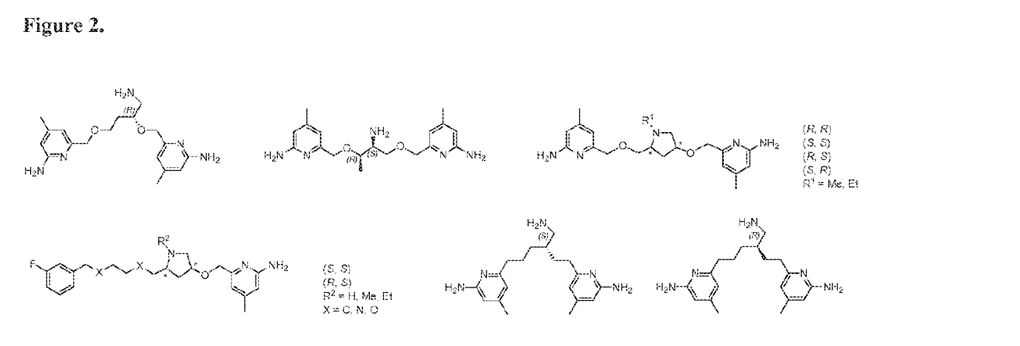

The following illustrates preparation and use of various NOS inhibitor compounds, in accordance with certain non-limiting embodiments of this invention. Using well-known synthetic techniques, as would be understood by those skilled in the art made aware of this invention, representative compounds 1-21 were prepared, as shown. Structural analogues of such compounds can be prepared using such techniques or straight-forward variations thereof, such analogous compounds limited only by commercial or synthetic availability of corresponding starting materials and reagents, such techniques, variations, starting materials and reagents as would also be understood by those skilled in the art and made aware of this invention. Many of the present compounds involve aminopyridine component 22, and its synthesis from available starting materials is described in Scheme 1. The synthesis of compound 1 starts from the commercially available resorcinol and reaction with N-protected bromide intermediate, generating compound 23. Coupling via an ether synthesis provided compound 24. The final product, compound 1, was obtained in a yield of 74% after deprotection.

Scheme 1.

Synthesis of compound 1

-continued

1

Scheme 2.

Synthesis of compound 2

2

With reference to scheme 2, ether synthesis was used to couple a pyridinyl fragment with resorcinol, and a second ether synthesis connected an aminopyridine component to the backbone. Compound 2 was obtained in a yield of 89% after removal of the dimethylpyrrole protecting group.

The structure and synthesis of compound 3 are similar to compound 2. As shown in scheme 3, Mitsunobu reaction linked a piperidinyl compound to the resorcinol linker, which was followed by an ether synthesis to generate compound 28. After the respective removal of the two protecting groups, the final compound 3 was obtained in a good yield.

Scheme 4.

Synthesis of compound 4

With reference to scheme 4, ether synthesis was used to first couple an aminopyridine component to the aldehyde linker. Reductive amination then produced compound 31. Compound 4 was obtained successfully after removing the protecting group.

Scheme 5.

Synthesis of compound 5

With reference to scheme 5, ether synthesis was first used to connect the aminopyridine component to the pyridinyl linker, then the methyl ester was reduced with Dibal-H to the aldehyde. Reductive amination produced compound 34. (Compounds incorporating a chlorophenyl moiety are available through use of a corresponding chloro-substituted amine.) Compound 5 was obtained successfully after removing the protecting group.

Scheme 6.

6

Compounds 6-9 were prepared using the same synthetic route, from their respective starting materials. For instance, as shown in Scheme 6, the commercially available proline analogue was reduced with LiBH₄ to generate diol 35. Then, a one-step ether synthesis linked two aminopyridine components to produce compound 36. The final compound 6 was obtained after the respective removal of the dimethylpyrrole and Boc protecting groups. Compounds 7-9 were synthesized via the same method with similar yields.

Scheme 7.

Synthesis of compound 10-11

-continued

41

1) NH₂OH•HCl, EtOH/H₂O
2) 2M HCl, dioxane/CH₃OH
73%

10

Compounds 10-11 were prepared using the same synthetic route, from their respective starting materials. As shown in scheme 7, a first intermediate compound 38 was prepared from 22 after ether synthesis with subsequent bromination. Second fragment compound 40 was synthesized through an ether synthesis and subsequent reduction with LiBH₄. Compounds 38 and 40 were coupled to produce 41, with compound 10 obtained after deprotection. Compound 11 was synthesized via the same method with similar yields.

Scheme 8.

Synthesis of compound 12-13

Compounds 12-13 were prepared using the same synthetic route, and share intermediate 40 with compounds 10-11. As shown in scheme 8, second intermediate compound 44 was prepared from 3-fluorophenylmethanol, with subsequent breakage of C=C bond, reduction to alcohol 43 and bromination. Compounds 44 and 40 were coupled via ether synthesis to produce 45, with compound 12 then obtained after deprotection. Compound 13 was synthesized via the same method in similar yield.

With reference to scheme 9, the diol starting material was first dimethylpyrrole protected, then coupled with two aminopyridine components via a one-step reaction to generate 47. The final compound 14 was obtained after the removal of the three protecting groups under the same conditions. Compound 15 was synthesized via the same method in similar yield.

With reference to Scheme 10, the synthesis of compound 16 started with an aminobutyric acid analogue. After reduction of the acid to alcohol and amino group protection, compound 49 was generated in good yield. Two aminopyridine components were coupled thereto via a one-step ether synthesis in a yield of 68%. Final compound 16 was obtained after the removal of the three protecting groups under the same conditions. Compound 17 was synthesized via the same method in similar yield.

Scheme 11.
Synthesis of compound 18

As shown in scheme 11, the synthesis of compound 18 followed the same synthetic method as used for compounds 16-17, from the corresponding aminobutyric acid starting material.

Scheme 12.
Synthesis of compound 19-21

-continued

19

The compounds, compositions and/or methods of the present invention can suitably comprise, consist of, or consist essentially of any of the aforementioned moieties or substituents and/or functional groups thereof. Each such compound or moiety/substituent/functional group thereof is compositionally distinguishable, characteristically contrasted and can be practiced in conjunction with the present invention separate and apart from another. Accordingly, it should also be understood that the inventive compounds, compositions and/or methods, as illustratively disclosed herein, can be claimed, practiced or utilized in the absence of any one compound, moiety/substituent/functional group which may or may not be disclosed, referenced or inferred herein, the absence of which may or may not be specifically disclosed, referenced or inferred herein.

With reference to scheme 12, compounds 19-21 were prepared using the same synthetic route, from their respective starting materials. After protection of the amino group, the methyl ester was reduced with $LiBH_4$ to the alcohol. The two aminopyridine components were coupled via a one-step ether synthesis in a yield of 73%. The final compound 19 was obtained after the removal of the three protecting groups under the same conditions. Compounds 20-21 were synthesized via the same method with similar yields.

Demonstrating utility of this invention, NOS inhibition assays of representative compounds 1-21 were undertaken, and the results are summarized in Table 1, below. All NOS isoforms were expressed and purified as described in U.S. Pat. No. 7,470,790 and the literature references cited therein, each of which is incorporated herein by reference in its entirety. Nitric oxide formation from NOS was monitored using literature techniques. Again, reference is made to the aforementioned '790 patent and the references cited therein. (See, e.g., Hevel, J. M.; Marletta, M. A. Nitric Oxide Synthase Assays. Methods Enzymol. 1994, 133, 250-258).

TABLE 1

Inhibition of NOS isozymes by synthetic inhibitors.[a]

| Compounds | Ki [nM] | | | Selectivity[b] | |
|---|---|---|---|---|---|
| | nNOS | eNOS | iNOS | e/n | i/n |
| 1 | 60 | 18018 | 8472 | 298 | 140 |
| 2 | 616 | 62832 | 27104 | 102 | 44 |
| 3 | 117 | 27963 | 17124 | 239 | 146 |
| 4 | 40 | 14414 | 9914 | 260 | 147 |
| 5 | 140 | 7114 | 2862 | 74 | 21 |
| 6 | 26 | 2179 | 2271 | 84 | 87 |
| 7 | 34 | 3473 | 5588 | 102 | 164 |
| 8 | 31 | 2356 | 1902 | 76 | 61 |
| 9 | 10 | 6927 | 2954 | 693 | 295 |
| 10 | 70 | 6248 | 2316 | 89 | 33 |
| 11 | 199 | 9300 | 13564 | 46 | 68 |
| 12 | 153 | 7963 | 5858 | 52 | 38 |
| 13 | 330 | 11726 | 8472 | 35 | 26 |
| 14 | 382 | 26446 | 40829 | 69 | 107 |

TABLE 1-continued

Inhibition of NOS isozymes by synthetic inhibitors.[a]

| Compounds | Ki [nM] | | | Selectivity[b] | |
|---|---|---|---|---|---|
| | nNOS | eNOS | iNOS | e/n | i/n |
| 15 | 32 | 15200 | 7808 | 475 | 244 |
| 16 | 1599 | 92742 | 52767 | 58 | 33 |
| 17 | 881 | 66957 | 31410 | 76 | 35 |
| 18 | 232 | 20197 | 10725 | 87 | 46 |
| 19 | 47 | 2995 | 1857 | 64 | 39 |
| 20 | 37 | 3042 | 2262 | 82 | 61 |
| 21 | 384 | 17678 | 10996 | 46 | 28 |

[a] $K_M$ values of rat nNOS, 1.3 μM; murine iNOS, 8.2 μM; bovine eNOS, 1.7 μM). $K_i = IC_{50}/(1 + [S]/K_M)$.
[b] The ratio of $K_i$ (eNOS or iNOS) to nNOS The present invention can also, as would be understood by those skilled in the art, be extended to or include methods using or in conjunction with a pharmaceutical composition comprising an inhibitor compound of the sort described herein and a physiologically or otherwise suitable formulation. In a some embodiments, the present invention includes one or more NOS inhibitors, as set forth above, formulated into compositions together with one or more physiologically tolerable or acceptable diluents, carriers, adjuvants or vehicles that are collectively referred to herein as carriers. Compositions suitable for such contact or administration can comprise physiologically acceptable sterile aqueous or non-aqueous solutions, dispersions, suspensions or emulsions. The resulting compositions can be, in conjunction with the various methods described herein, for administration or contact with a nitric oxide synthase. Whether or not in conjunction with a pharmaceutical composition, "contacting" means that a nitric oxide synthase and one or more inhibitor compounds are brought together for purpose of binding and/or complexing such an inhibitor compound to the enzyme. Amounts of a compound effective to inhibit a nitric oxide synthase may be determined empirically, and making such determinations is within the skill in the art. Inhibition or otherwise affecting nitric oxide synthase activity includes modulation, reduction and/or mitigation, as well as elimination of NOS activity and/or nitric oxide production.

It is understood by those skilled in the art that dosage amount will vary with the activity of a particular inhibitor compound, disease state, route of administration, duration of treatment, and like factors well-known in the medical and pharmaceutical arts. In general, a suitable dose will be an amount which is the lowest dose effective to produce a therapeutic or prophylactic effect. If desired, an effective dose of such a compound, pharmaceutically-acceptable salt thereof, or related composition may be administered in two or more sub-doses, administered separately over an appropriate period of time.

Methods of preparing pharmaceutical formulations or compositions include the step of bringing an inhibitor compound into association with a carrier and, optionally, one or more additional adjuvants or ingredients. For example, standard pharmaceutical formulation techniques can be employed, such as those described in Remington's Pharmaceutical Sciences, Mack Publishing Company, Easton, Pa.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the present invention provides for use of one or more neuronal nitric oxide synthase inhibitor compounds for the manufacture of a medicament for therapeutic use in the treatment or prevention of a disease state indicated by nitric oxide production.

EXAMPLES OF THE INVENTION

The following non-limiting examples and data illustrate various aspects and features relating to the compounds and/or methods of the present invention, including the preparation of selective NOS inhibitor compounds, as available through the synthetic methodologies described herein. In comparison with the prior art, the present compounds, compositions and methods provide results and data which are surprising, unexpected and contrary thereto. While the utility of this invention is illustrated through the use of several compounds and structural moieties which can be incorporated therein, it will be understood by those skilled in the art that comparable results are obtainable with various other structurally analogous compounds and incorporated moieties, as are commensurate with the scope of this invention.

With reference to the preceding synthetic schemes, the following examples provide spectroscopic and related data characterizing the indicated compounds.

Example 1

Compound 1: M.p. 96-98° C. $^1$H NMR (500 MHz, CDCl$_3$) δ 1.88-1.94 (m, 2H), 2.23 (s, 3H), 2.90 (t, J=6.5 Hz, 2H), 4.03 (t, J=6.5 Hz, 2H), 4.36 (br, 2H), 4.95 (s, 2H), 6.25 (s, 1H), 6.51 (d, J=7.0 Hz, 1H), 6.56-6.58 (m, 2H), 6.69 (s, 1H), 7.16 (t, J=8.5 Hz, 1H); $^{13}$C NMR (125 MHz, CDCl$_3$) δ 21.1, 33.0, 39.3, 65.8, 70.6, 101.7, 106.9, 107.2, 108.0, 112.9, 129.8, 149.7, 155.1, 158.1, 159.8, 160.1 ppm; MS (ESI): 288.3 (M+H)$^+$. HRMS (ESI): calcd. 288.1712. Found: 288.1717.

Example 2

Compound 2: M.p. 97-99° C. $^1$H NMR (500 MHz, CDCl$_3$) δ 2.23 (s, 6H), 4.41 (br, 2H), 4.95 (s, 2H), 5.07 (s, 2H), 6.26 (s, 1H), 6.57 (d, J=7.0 Hz, 1H), 6.61-6.63 (m, 2H), 6.67 (s, 1H), 7.18 (t, J=8.0 Hz, 1H), 7.33 (d, J=5.5 Hz, 2H), 8.60 (d, J=5.5 Hz, 2H); $^{13}$C NMR (125 MHz, CDCl$_3$) δ 21.1, 68.1, 70.6, 102.1, 107.4, 107.7, 108.1, 112.9, 130.1, 146.2, 149.7, 150.0, 154.8, 158.2, 159.3, 159.9 ppm; MS (ESI): 322.3 (M+H)$^+$. HRMS (ESI): calcd. 322.1556. Found: 322.1552 (M+H)$^+$.

Example 3

Compound 3: white solid 62 mg. 94%. M.p. 103-105° C. $^1$H NMR (500 MHz, DMSO) δ 1.67-1.76 (m, 4H), 2.13 (s, 3H), 2.42-2.45 (m, 1H), 2.93 (d, J=11.5 Hz, 2H), 3.74 (d, J=6.5 Hz, 2H), 4.83 (s, 2H), 5.82 (s, 2H), 6.18 (s, 1H), 6.44 (s, 1H), 6.51 (t, J=7.5 Hz, 1H), 7.13 (t, J=7.5 Hz, 1H), 8.29 (s, 2H); $^{13}$C NMR (125 MHz, CDCl$_3$) δ 20.7, 29.8, 36.0, 45.7, 70.2, 72.5, 101.2, 106.7, 106.8, 107.1, 110.6, 129.8, 147.8, 154.4, 154.5, 159.5, 159.9 ppm; MS (ESI): 328.4 (M+H)$^+$. HRMS (ESI): calcd. 328.2025. Found: 328.2027 (M+H)$^+$.

Example 4

Compound 4: M.p. 137-139° C. $^1$H NMR (500 MHz, CDCl$_3$) δ 2.23 (s, 3H), 2.81 (t, J=7.0 Hz, 2H), 2.88 (t, J=7.0 Hz, 2H), 3.77 (s, 2H), 4.37 (br, 2H), 4.96 (s, 2H), 6.25 (s, 1H), 6.70 (s, 1H), 6.85-6.91 (m, 4H), 6.94 (s, 1H), 6.97 (d, J=7.5

Hz, 1H), 7.20-7.24 (m, 2H); $^{13}$C NMR (125 MHz, CDCl$_3$) δ 21.14, 36.12, 50.08, 53.72, 70.44, 107.98, 112.91+112.94, 113.11, 113.19, 114.55, 115.42+115.59, 120.60, 124.36, 124.38, 129.41+129.79, 129.85, 141.79, 142.57+142.63, 149.72, 155.14, 158.10, 158.76 ppm. MS (ESI): 366.4 (M+H)$^+$. HRMS (ESI): calcd. 366.1982. Found: 366.1980 (M+H)$^+$.

Example 5

Compound 5: M.p. 128-130° C. $^1$H NMR (500 MHz, CDCl$_3$) δ 2.23 (s, 6H), 2.45 (s, 3H), 2.80 (t, J=6.5 Hz, 2H), 2.86 (t, J=6.5 Hz, 2H), 3.79 (s, 2H), 5.00 (s, 2H), 6.26 (s, 1H), 6.65 (s, 1H), 6.88-6.91 (m, 2H), 6.96 (d, J=7.0 Hz, 1H), 7.22-7.26 (m, 2H), 8.14 (s, 1H), 8.28 (s, 1H); $^{13}$C NMR (125 MHz, CDCl$_3$) δ 21.86, 36.03, 50.03, 50.83, 70.57, 108.39, 112.89, 113.09+113.25, 115.46+115.63, 121.15, 124.38, 129.90+129.96, 136.22, 137.14, 142.01, 142.34+142.40, 149.97, 154.00, 154.87, 155.62, 158.34 ppm. MS (ESI): 367.5 (M+H)$^+$. HRMS (ESI): calcd. 367.1934. Found: 367.1939 (M+H)$^+$.

Example 6

Compound 6: M.p. 124-126° C. $^1$H NMR (500 MHz, CDCl$_3$) δ 6.61 (s, 1H), 6.57 (s, 1H), 6.23 (s, 2H), 4.43 (q, J=10.0 Hz, J=5.0 Hz, 4H), 4.36 (d, J=5.0 Hz, 4H), 4.18-4.16 (m, 1H), 3.69-3.64 (m, 1H), 3.55-3.49 (m, 2H), 3.13-3.11 (m, 2H), 2.24 (s, 3H), 2.23 (s, 3H), 2.08 (dd, J=14.0 Hz, J=5.0 Hz, 1H), 1.73-1.67 (m, 1H); $^{13}$C NMR (126 MHz, CDCl$_3$) δ 158.27, 158.12, 156.39, 156.24, 149.58, 149.55, 113.10, 112.97, 107.86, 107.81, 80.30, 73.76, 71.63, 56.68, 52.02, 45.99, 34.96, 21.12 ppm; MS (ESI): 358.4 (M+H)$^+$. HRMS (ESI): calcd. 358.2243. Found: 358.2234 (M+H)$^+$.

Example 7

Compound 7: M.p. 126-128° C. $^1$H NMR (500 MHz, CDCl$_3$) δ 6.60 (s, 1H), 6.59 (s, 1H), 6.22 (s, 2H), 4.45 (m, 2H), 4.37 (s, 2H), 4.39-4.35 (m, 1H), 3.78-3.74 (m, 1H), 3.65-3.60 (m, 2H), 3.49-3.44 (m, 1H), 3.18 (d, J=10.0 Hz, 1H), 2.98-2.94 (m, 1H), 2.21 (s, 6H), 2.18 (dd, J=10.0 Hz, J=5.0 Hz, 1H), 1.69-1.65 (m, 1H); $^{13}$C NMR (126 MHz, CDCl$_3$) δ 158.17, 158.09, 156.34, 156.23, 149.54, 112.97, 112.94, 107.80, 107.75, 80.08, 73.71+73.57, 71.61, 57.63, 52.23, 42.91, 35.05, 21.10, 21.08 ppm; MS (ESI): 358.4 (M+H)$^+$. HRMS (ESI): calcd. 358.2243. Found: 358.2242 (M+H)$^+$.

Example 8

Compound 8: M.p. 124-126° C. $^1$H NMR (500 MHz, CDCl$_3$) δ 6.60 (s, 1H), 6.59 (s, 1H), 6.22 (s, 2H), 4.45 (m, 2H), 4.37 (s, 2H), 4.39-4.35 (m, 1H), 3.78-3.74 (m, 1H), 3.65-3.60 (m, 2H), 3.49-3.44 (m, 1H), 3.18 (d, J=10.0 Hz, 1H), 2.98-2.94 (m, 1H), 2.21 (s, 6H), 2.18 (dd, J=10.0 Hz, J=5.0 Hz, 1H), 1.69-1.65 (m, 1H); $^{13}$C NMR (126 MHz, CDCl$_3$) δ 158.17, 158.09, 156.34, 156.23, 149.54, 112.97, 112.94, 107.80, 107.75, 80.08, 73.71+73.57, 71.61, 57.63, 52.23, 42.91, 35.05, 21.10, 21.08 ppm; MS (ESI): 358.4 (M+H)$^+$. HRMS (ESI): calcd. 358.2243. Found: 358.2236 (M+H)$^+$.

Example 9

Compound 9: M.p. 126-128° C. $^1$H NMR (500 MHz, CDCl$_3$) δ 6.61 (s, 1H), 6.57 (s, 1H), 6.23 (s, 2H), 4.43 (q, J=10.0 Hz, 4H), 4.36 (d, J=5.0 Hz, 4H), 4.18-4.16

(m, 1H), 3.69-3.64 (m, 1H), 3.55-3.49 (m, 2H), 3.13-3.11 (m, 2H), 2.24 (s, 3H), 2.23 (s, 3H), 2.08 (dd, J=14.0 Hz, J=5.0 Hz, 1H), 1.73-1.67 (m, 1H); $^{13}$C NMR (126 MHz, CDCl$_3$) δ 158.29, 158.18, 156.37, 156.28, 149.54, 149.51, 112.99, 112.82, 107.88, 107.82, 80.20, 73.67, 71.58, 56.66, 51.88, 45.90, 34.89, 21.10 ppm; MS (ESI): 358.4 (M+H)$^+$. HRMS (ESI): calcd. 358.2234. Found: 358.2238.

Example 10

Compound 10: M.p. 136-138° C. $^1$H NMR (500 MHz, CDCl$_3$) δ 6.49 (s, 2H), 6.26 (s, 2H), 4.46-4.30 (m, 6H), 3.78-3.67 (m, 6H), 3.43-3.28 (m, 2H), 2.94-2.78 (m, 1H), 2.22 (s, 3H), 2.20 (s, 3H), 2.18-2.12 (m, 1H); $^{13}$C NMR (126 MHz, CDCl$_3$) δ 158.46, 158.29, 154.15, 153.68, 150.57, 150.38, 128.43, 113.28+113.14, 113.06+112.95, 108.88, 108.74, 78.30, 72.88, 70.68, 70.55, 69.81, 57.37, 50.06, 45.30, 36.76, 28.48, 21.17, 21.15 ppm; MS (ESI): 402.7 (M+H)$^+$. calcd. 402.2505. Found: 402.2492 (M+H)$^+$.

Example 11

Compound 11: pale yellow solid 15 mg, 73%. M.p. 139-141° C. $^1$H NMR (500 MHz, CDCl$_3$) δ 6.55-6.51 (m, 2H), 6.21 (s, 2H), 4.45-4.35 (m, 4H), 4.22 (s, 1H), 3.72-3.59 (m, 8H), 3.37-3.08 (m, 2H), 2.22 (s, 3H), 2.21 (s, 3H), 2.05-2.02 (m, 1H); $^{13}$C NMR (126 MHz, CDCl$_3$) δ 158.55, 158.37, 155.38, 153.20, 149.93, 149.77, 113.16, 112.92, 108.25, 108.23, 79.34+78.92, 73.54, 72.43, 71.09, 70.53, 69.90, 57.04+56.82, 53.47, 50.99, 50.47, 34.20, 29.43, 21.12 ppm; MS (ESI): 402.8 (M+H)$^+$. calcd. 402.2505. Found: 402.2498 (M+H)$^+$.

Example 12

Compound 12: M.p. 137-139° C. $^1$H NMR (500 MHz, CDCl$_3$) δ 7.29-7.26 (m, 1H), 7.10-7.06 (m, 2H), 6.96 (t, J=7.0 Hz, 1H), 6.55 (s, 1H), 6.22 (s, 1H), 4.55 (s, 2H), 4.41-4.39 (m, 2H), 3.68-3.56 (m, 6H), 3.50-3.47 (m, 2H), 3.47-3.10 (m, 2H), 2.22 (s, 3H), 2.06 (dd, J=6.5 Hz, J=13.5 Hz, 1H), 1.74-1.71 (m, 1H); $^{13}$C NMR (126 MHz, CDCl$_3$) δ 163.91, 161.95, 158.30, 149.86, 140.98+140.92, 129.91+129.84, 122.98, 114.50+114.42+114.33+114.24, 112.91, 108.12, 79.88, 73.20+73.11, 72.36, 71.06, 70.54, 69.62+69.56, 56.57, 51.42, 34.70+34.60, 21.10 ppm; MS (ESI): 390.7 (M+H)$^+$. HRMS (ESI) calcd. 390.2193. Found: 390.2198 (M+H)$^+$.

Example 13

Compound 13: M.p. 139-141° C. $^1$H NMR (500 MHz, CDCl$_3$) δ 7.29-7.26 (m, 1H), 7.08 (d, J=7.5 Hz, 1H), 7.05 (d, J=7.5 Hz, 1H), 6.96 (t, J=7.5 Hz, 1H), 6.52 (s, 1H), 6.21 (s, 1H), 4.54 (s, 4H), 4.41-4.20 (m, 2H), 3.70 (br, 1H), 3.69-3.63 (m, 4H), 3.58-3.53 (m, 1H), 3.26 (d, J=11.0 Hz, 1H), 3.02-2.99 (m, 1H), 2.21 (s, 3H), 2.17-2.15 (m, 2H); $^{13}$C NMR (126 MHz, CDCl$_3$) δ 163.88, 161.93, 158.32, 155.64+155.50, 149.85, 140.94+140.88, 129.91+129.84, 123.02, 114.49+114.45+114.32+114.28, 112.90+112.84, 108.13, 79.38, 73.07, 72.44, 71.05, 70.50, 69.62+69.55, 61.91, 57.02, 51.08, 34.59, 21.08 ppm; MS (ESI): 390.7 (M+H)$^+$. calcd. 390.2193. Found: 390.2192 (M+H)$^+$.

Example 14

Compound 14: M.p. 133-135° C. $^1$H NMR (500 MHz, CDCl$_3$) δ 6.50 (s, 1H), 6.45 (s, 1H), 6.20 (s, 2H), 4.71 (br, 2H), 4.63-4.44 (m, 2H), 4.41-4.37 (m, 2H), 3.76-3.65 (m, 3H), 3.19-2.99 (m, 2H), 2.78 (br, 4H), 2.19 (s, 6H); $^{13}$C NMR (126 MHz, CDCl$_3$) δ 158.77, 155.62, 155.41, 149.57, 149.43, 112.96, 112.63, 108.30, 108.06, 77.95, 73.65, 72.28, 71.59, 41.39, 21.02 ppm; MS (ESI): 332.7 (M+H)$^+$. HRMS (ESI): calcd. 332.2087. Found: 332.2081 (M+H)$^+$.

Example 15

Compound 15: M.p. 128-130° C. $^1$H NMR (500 MHz, CDCl$_3$) δ 6.61 (s, 1H), 6.55 (s, 1H), 6.22 (s, 2H), 6.80 (s, 1H), 4.63-4.50 (m, 4H), 4.46 (d, J=6.5 Hz, 1H), 3.67 (s, 2H), 2.93-2.89 (m, 2H), 2.21 (s, 6H); $^{13}$C NMR (126 MHz, CDCl$_3$) δ 158.34, 158.32, 156.30, 156.00, 149.52, 149.47, 113.15, 112.91, 107.95, 107.87, 79.50, 73.93, 72.58, 71.07, 42.78, 21.07 ppm; MS (ESI): 332.3 (M+H)$^+$. HRMS: (ESI): calcd. 332.2087. Found: 332.2082 (M+H)$^+$.

Example 16

Compound 16: M.p. 133-135° C. $^1$H NMR (500 MHz, CDCl$_3$) δ 6.57 (s, 1H), 6.50 (s, 1H), 6.22 (s, 1H), 6.19 (s, 1H), 4.66 (d, J=12.5 Hz, 1H), 4.49 (d, J=12.5 Hz, 1H), 4.45 (s, 3H), 3.79-3.76 (m, 1H), 3.01-2.92 (m, 3H), 2.22 (s, 3H), 2.19 (s, 3H), 1.85-1.81 (m, 2H); $^{13}$C NMR (126 MHz, CDCl$_3$) δ 158.55, 158.28, 156.15, 156.10, 149.49, 149.47, 112.93, 112.87, 108.00, 107.85, 77.89, 74.11, 72.83, 72.31, 38.50, 30.99, 21.11, 21.06 ppm. MS (ESI): 346.7 (M+H)$^+$. HRMS: (ESI): calcd. 346.2243. Found: 332.2250 (M+H)$^+$.

Example 17

Compound 17: M.p. 137-140° C. $^1$H NMR (500 MHz, CDCl$_3$) δ 6.57 (s, 1H), 6.50 (s, 1H), 6.22 (s, 1H), 6.19 (s, 1H), 4.66 (d, J=12.5 Hz, 1H), 4.49 (d, J=12.5 Hz, 1H), 4.45 (s, 3H), 3.79-3.76 (m, 1H), 3.01-2.92 (m, 3H), 2.22 (s, 3H), 2.19 (s, 3H), 1.85-1.81 (m, 2H); $^{13}$C NMR (126 MHz, CDCl$_3$) δ 158.65, 158.48, 156.17, 156.13, 149.49, 149.47, 112.93, 112.87, 108.00, 107.89, 77.88, 74.11, 72.83, 72.31, 38.50, 30.99, 21.11, 21.06 ppm. MS (ESI): 346.5 (M+H)$^+$. HRMS: (ESI): calcd. 346.2243. Found: 346.2245 (M+H)$^+$.

Example 18

Compound 18: M.p. 134-136° C. $^1$H NMR (500 MHz, CDCl$_3$) δ 6.50 (s, 1H), 6.46 (s, 1H), 6.21 (s, 1H), 6.22 (s, 1H), 4.52 (d, J=12.5 Hz, 1H), 4.42-4.37 (m, 3H), 3.67-3.64 (m, 1H), 3.62-3.57 (m, 2H), 3.08 (dd, J=10.0 Hz, J=5.0 Hz, 1H), 2.88 (dd, J=10.0 Hz, J=5.0 Hz, 1H), 2.20 (s, 3H), 2.18 (s, 3H), 1.96-1.1.88 (m, 2H); $^{13}$C NMR (126 MHz, CDCl$_3$) δ 158.64, 158.55, 155.89, 155.77, 149.62, 149.46, 112.99, 112.88, 108.24, 108.05, 73.72, 72.31, 66.73, 43.62, 32.88, 21.06 ppm. MS (ESI): 346.7 (M+H)$^+$. HRMS: (ESI): calcd. 346.2243. Found: 346.2241 (M+H)$^+$.

Example 19

Compound 19: M.p. 127-129° C. $^1$H NMR (500 MHz, CDCl$_3$) δ 6.48 (s, 1H), 6.46 (s, 1H), 6.22 (s, 1H), 6.21 (s, 1H), 4.59 (d, J=10.0 Hz, 1H), 4.48-4.35 (m, 3H), 3.69-3.62 (m, 2H), 3.07-3.05 (m, 1H), 2.76-2.72 (m, 1H), 2.21 (s, 6H), 1.23 (d, J=5.0 Hz, 3H); $^{13}$C NMR (126 MHz, CDCl$_3$) δ 158.52, 158.37, 156.21, 156.76, 149.62, 149.59, 112.73, 112.52, 108.09, 107.92, 76.32, 73.36, 71.17, 56.20, 50.81, 21.08, 21.05, 16.26 ppm. MS (ESI): 346.2 (M+H)$^+$. HRMS: (ESI): calcd. 346.2243. Found: 332.2241, (M+H)$^+$.

Example 20

Compound 20: M.p. 125-127° C. $^1$H NMR (500 MHz, CDCl$_3$) δ 6.48 (s, 1H), 6.46 (s, 1H), 6.22 (s, 1H), 6.21 (s, 1H),

4.59 (d, J=10.0 Hz, 1H), 4.48-4.35 (m, 3H), 3.69-3.62 (m, 2H), 3.07-3.05 (m, 1H), 2.76-2.72 (m, 1H), 2.21 (s, 6H), 1.23 (d, J=5.0 Hz, 3H); $^{13}$C NMR (126 MHz, CDCl$_3$) δ 158.52, 158.37, 156.21, 156.76, 149.62, 149.59, 112.73, 112.52, 108.09, 107.92, 76.32, 73.36, 71.17, 56.20, 50.81, 21.08, 21.05, 16.26 ppm. MS (ESI): 346.2 (M+H)$^+$. HRMS: (ESI): calcd. 346.2243. Found: 332.2239 (M+H)$^+$.

Example 21

Compound 21: M.p. 129-132° C. $^1$H NMR (500 MHz, CDCl$_3$) δ 6.54 (s, 2H), 6.22 (s, 1H), 6.21 (s, 1H), 4.53-4.35 (m, 5H), 3.73-3.70 (m, 2H), 3.51-3.47 (m, 1H), 2.21 (s, 6H), 1.23 (d, J=5.0 Hz, 3H); $^{13}$C NMR (126 MHz, CDCl$_3$) δ 158.28, 158.19, 156.60, 156.51, 149.53, 149.51, 112.90, 112.76, 107.88, 107.79, 73.77, 72.29, 71.35, 54.65, 21.10, 21.08, 15.29 ppm. MS (ESI): 346.2 (M+H)$^+$. HRMS: (ESI): calcd. 346.2243 (M+H)$^+$. Found: 332.2243, (M+H)$^+$.

We claim:
1. A compound selected from compounds of a formula wherein R$^1$ is selected from 6-aminopyridin-2-yl and 6-amino-4-methylpyridin-2-yl moieties; X is selected from CH$_2$O, CH$_2$CH$_2$ and CH$_2$OCH$_2$ moieties; Y is selected from O and CH$_2$ moieties; and n is an integer selected from 1 and 2, and salts thereof.

2. The compound of claim 1 wherein R$^1$ is a 6-amino-4-methylpyridin-2-yl moiety.

3. The compound of claim 2 wherein X is selected from CH$_2$O and CH$_2$OCH$_2$ moieties.

4. The compound of claim 2 wherein n is 1.

5. The compound of claim 1 wherein said compound is an ammonium salt.

6. The compound of claim 4 wherein said ammonium salt has a counter ion that is a conjugate base of a protic acid.

* * * * *